United States Patent
Marrgi et al.

(10) Patent No.: US 6,620,138 B1
(45) Date of Patent: Sep. 16, 2003

(54) INFUSOR, CATHETER MEANS AND CATHETER HEAD

(75) Inventors: Rolf Marrgi, Bern (CH); Willi Michel, Burgdorf (CH); Jürg Steck, Kirchberg (CH)

(73) Assignee: Disetronic Licensing AG, Burgdorf (CH)

(*) Notice: Subject to any disclaimer, the term of this patent is extended or adjusted under 35 U.S.C. 154(b) by 0 days.

(21) Appl. No.: 09/528,079

(22) Filed: Mar. 17, 2000

(30) Foreign Application Priority Data

Mar. 19, 1999 (DE) .......................... 199 12 434

(51) Int. Cl.[7] .............................. A61M 5/00
(52) U.S. Cl. ........................ 604/264; 604/110
(58) Field of Search .................. 604/264, 30, 93.01, 604/158, 164.01, 110, 165.01, 174, 167.01, 539, 180, 240–242, 284, 283, 272, 243, 905

(56) References Cited

U.S. PATENT DOCUMENTS

| | | | |
|---|---|---|---|
| 2,112,160 A | * 3/1938 | Johnson | 128/2 |
| 3,767,085 A | * 10/1973 | Cannon et al. | 222/82 |
| 4,044,757 A | * 8/1977 | McWhorter et al. | 128/2 |
| 4,436,519 A | 3/1984 | O'Neill | 604/175 |
| 4,682,981 A | 7/1987 | Suzuki et al. | 604/158 |
| 4,755,173 A | * 7/1988 | Konopka et al. | 604/167 |
| 4,880,412 A | 11/1989 | Weiss | 604/165 |
| 4,886,501 A | 12/1989 | Johnston et al. | 604/175 |
| 4,966,588 A | 10/1990 | Rayman et al. | 604/165 |
| 5,092,849 A | 3/1992 | Sampson | 604/175 |
| 5,098,398 A | 3/1992 | Lundgren | 604/175 |
| 5,281,199 A | 1/1994 | Ensminger et al. | 604/93 |
| 5,429,609 A | 7/1995 | Yoon | 604/167 |
| 5,522,803 A | 6/1996 | Teissen-Simony | 604/177 |
| 5,545,143 A | * 8/1996 | Fischell | |
| 5,584,815 A | 12/1996 | Pawelka et al. | 604/191 |
| 5,634,911 A | 6/1997 | Hermann et al. | 604/256 |
| 5,634,937 A | 6/1997 | Mollenauer et al. | 606/213 |
| 5,788,673 A | 8/1998 | Young et al. | 604/131 |
| 5,827,244 A | 10/1998 | Boettger | 604/283 |
| 5,875,928 A | 3/1999 | Müller et al. | 222/82 |
| 5,954,687 A | 9/1999 | Baudino | 604/48 |
| 5,975,367 A | 11/1999 | Coelho et al. | 222/137 |
| 6,047,861 A | 4/2000 | Vidal et al. | 222/137 |
| 6,071,265 A | 6/2000 | Bestetti et al. | 604/256 |

FOREIGN PATENT DOCUMENTS

| | | |
|---|---|---|
| DE | 1491841 | 7/1969 |
| EP | 0045339 | 2/1982 |
| EP | 0298067 | 10/1991 |

* cited by examiner

*Primary Examiner*—Manuel Mendez
(74) *Attorney, Agent, or Firm*—Dorsey & Whitney LLP

(57) ABSTRACT

The present invention provides an infusor including a housing, a reservoir accommodated in the housing for containing a product fluid to be administered, and a delivery means accommodated in the housing for an automatic dosed delivery of the product fluid from the reservoir, wherein the reservoir includes at least two separate fluid spaces having separate fluid outlets.

12 Claims, 5 Drawing Sheets

INFUSOR, CATHETER MEANS AND CATHETER HEAD

BACKGROUND OF THE INVENTION

This application claims the priority of German patent application no. 199 12 434.5, filed Mar. 19, 1999, which is incorporated herein by reference.

FIELD OF THE INVENTION

The invention relates to an infusor for the dosed administration of a product fluid as well as a catheter means and a catheter head used, more particularly, together with the infusor.

The object of the invention is to facilitate administering a product fluid, especially for the case of a user himself administering the product.

SUMMARY

An infusor of the kind relating to the invention comprises a housing accommodating a reservoir for at least one product fluid to be administered and a delivery means accommodated in the housing for dosed delivery of the product fluid from the reservoir. The product fluid is a solution of an active substance; preferably being a solution effective in medicine or in cosmetics. More particularly, it may involve insulin administered in the scope of diabetes therapy. Accordingly, the invention is described in the following by way of insulin therapy as an example.

In accordance with the invention, the product fluid is contained in at least two separate fluid spaces having separate fluid outlets. The reservoir is thus formed by at least these two fluid spaces or comprises at least two such fluid spaces separate from each other. Separating the fluid spaces makes it possible, more particularly, to automatically administer different product fluids, for example normal insulin, so-called pump insulin, and a quick-acting insulin as compared to the latter, more particularly insulin analog, using a single infusor. This results in the therapy being improved and simplified since the user administering himself no longer needs to implement injections manually, for example at unscheduled mealtimes or sports activities, thus eliminating the awkwardness and uncertainty involved in administration.

The infusor facilitates, in principle, not only the administration of different product fluids. When the at least two separate fluid spaces constitute conventional ampules, such those as employed many applications, by preparing the infusor so as to accommodate at least two such ampules, the amount of fluid which can be administered is increased by easily changing both ampules, preferably simultaneously. However, a primary use of the invention is regarded as administering different product fluids by a single infusor.

The delivery means is preferably configured so that each product fluid contained in the at least two separate fluid spaces can be alternatively delivered, i.e. both singly and together with the other. The two differing product fluids may be administered in a coordinated manner with each other, depending on the particular requirements of the treatment and of the user. Administration can thus be adapted as regards both quantity and time to at least two differing product fluids as ensured by a controller for the delivery means, preferably a programmable controller.

Connectable to the infusor is a catheter means comprising preferably at least one separate fluid conduit for each of the at least two separate fluid spaces. In this way, differing product fluids can be conducted—without becoming mixed—directly to an outlet or at least in the vicinity of an outlet forming an outlet common to the product fluids in the at least two separate fluid spaces.

In one catheter means, the separate fluid conduits form together an integral multilumen catheter body. The catheter body is prepared at one end for connection to the at least two separate fluid spaces. The other end of the catheter body is prepared for connection to a catheter head or is already commercially available with a catheter head.

In principle, each of the separate fluid conduits may be connected to a separate catheter head, a catheter head in accordance with the invention being preferred, however. Such a catheter head comprises a catheter head housing including a substantially flat underside suitable for direct skin contact and prepared for being attached to the skin. Furthermore, the catheter head comprises a piercing needle protruding from the underside of the catheter head housing. The catheter head is characterized by a fluid guide means being formed therein comprising an outlet and at least two inlets. The outlet is connected to the piercing needle, and the at least two inlets are each connectable to a product administering device. Two or more fluid conduits may be simply brought together in the catheter head. Preferably, the fluid guide means comprises a fluid chamber in the sense of an expanded fluid space into which a plurality of fluid conduits port.

In one embodiment, at least one inlet of the fluid guide means of the catheter head is closed off by a septum, which needs to be punctured by a connecting needle to connect to the product administering device whereby a hermetic seal forms around the connecting needle at the puncture site.

The connecting needle may be configured at a needle holder of a two-part catheter head, such a needle holder forming a removable part of the catheter head.

In one embodiment, the inlet of the fluid guide means of the catheter head hermetically sealed off by means of the septum is arranged in the catheter head such that it is suitable for connecting an injector, more particularly an injector pen. In this case, the injector forms one of the product administering devices. In this further development of the invention, the catheter head may serve as the catheter head for the infusor, as well as for an injector connected from time to time as required by the user and which makes use of the piercing needle or one of the piercing needles of the catheter head for administering its product fluid. In this configuration, in which a possibility for connecting an injector is provided, different product fluids may also be administered by means of the catheter head in accordance with the invention, even when the connected infusor comprises one fluid space only. With the then conventional infusor normal pump insulin, for example, may be administered and with the injector a quick-acting insulin or also a delayed-action insulin may be administered.

Exemplary embodiments will now be described with reference to the Figures.

BRIEF DESCRIPTION OF THE DRAWINGS

FIG. 2b is a side view of the infusor as shown in FIG. 2a.

FIG. 2c is a plan view of the infusor as shown in FIG. 2a.

FIG. 2d is a cross-sectional view of the infusor as shown in FIG. 2a.

FIG. 3 is a longitudinal section through the catheter head as shown in FIG. 2a.

DETAILED DESCRIPTION

The accompanying Figures and this description depict and describe embodiments of the infusor, catheter means and catheter head and method of the present invention, and features and components thereof. Fastening, mounting, attaching or connecting the components of the present invention to form the device as a whole, unless specifically described otherwise, are intended to encompass conventional fasteners such as machine screws, nut and bolt connectors, machine threaded connectors, snap rings, hose clamps such as screw clamps and the like, rivets, nuts and bolts, toggles, pins and the like. Components may also be connected by welding, friction fitting or deformation, if appropriate. Electrical connections, if any, may be made using appropriate electrical components and connection methods, including, but not limited to, conventional components and connectors. The microprocessor or controller for the present invention can be any digital controller or microprocessor-based system, and more than one may be involved. Unless specifically otherwise disclosed or taught, materials for making components of the present invention are selected from appropriate materials such as metal, metallic alloys, fibers, plastics and the like, and appropriate manufacturing or production methods including casting, extruding, molding and machining may be used.

Any references to front and back, right and left, top and bottom and upper and lower are intended for convenience of description, not to limit the present invention or its components to any one positional or spacial orientation. In the Figures, elements common to the embodiments of the invention are commonly identified.

Figure 1:
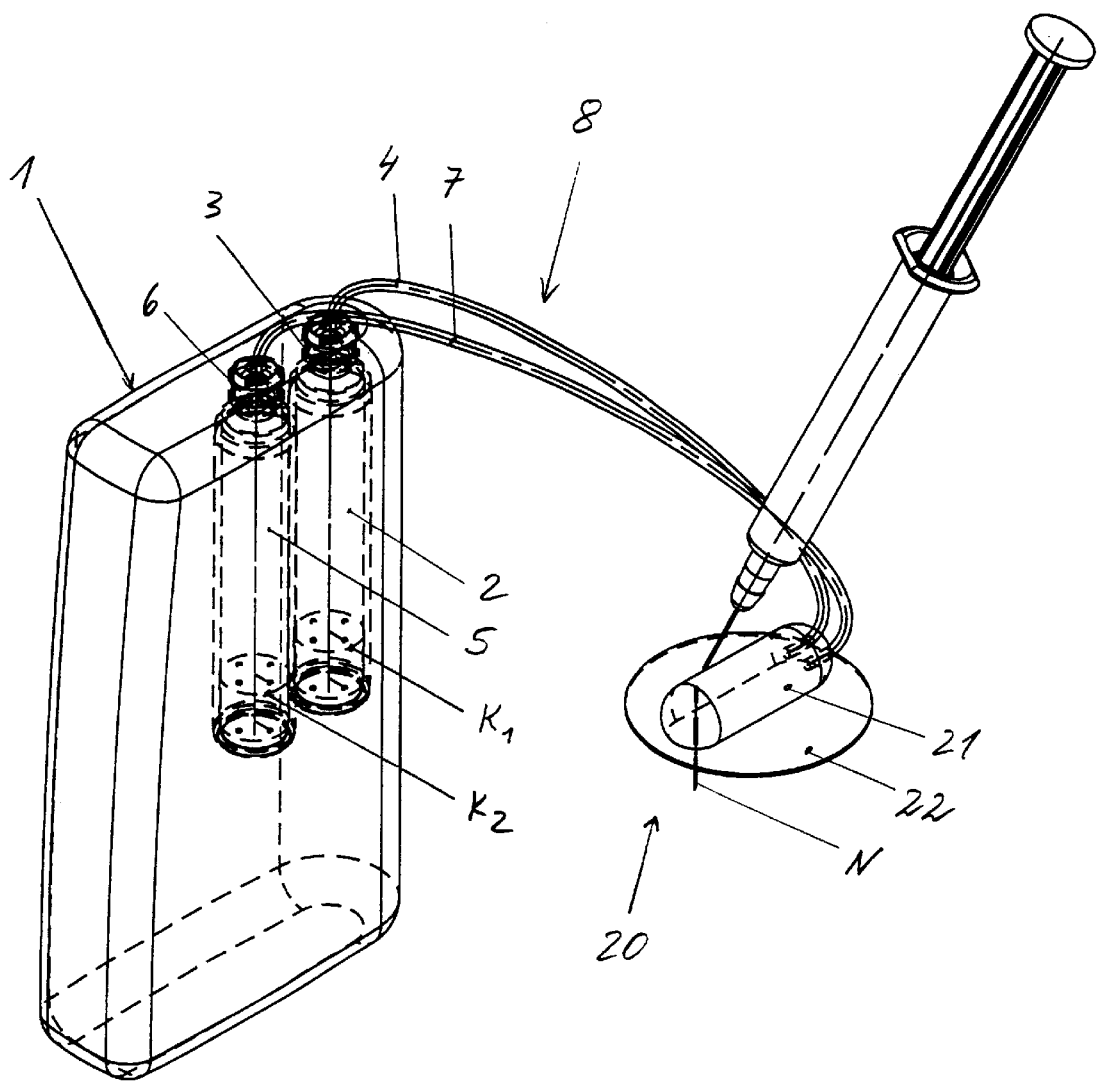
FIG. 1 is a view in perspective of a first example embodiment of an infusor, a connected catheter means and a catheter head.

Referring now to FIG. 1, there is illustrated a first examplary embodiment of an infusor including two separate product fluid spaces.

In a housing 1 of the infusor a first ampule 2 and a second ampule 5 are arranged adjacently parallel in a receiving chute. The receiving chute comprising straight guides for each of the ampules 2 and 5 or is formed itself by two separate individual chutes. Each of the two ampules 2 and 5 forms a separate product fluid space, i.e., a space closed off from the other space respectively, for the product fluid accommodated therein.

In the examplary embodiment, each of the two product fluids is formed by an insulin solution. The first ampule 2 contains normal pump insulin, whereas the second ampule 5 contains an insulin which as compared to the latter acts faster, so-called insulin analog. Each of the two ampules 2 and 5 may be formed by a conventional syringe ampule. Accommodated in ampule 2 is a piston K1 and in ampule 5 a piston K2 which are advanced to the corresponding ampule outlet 3 and 6 respectively by means of a delivery means, preferably comprising motor-powered spindle drives to dispense the corresponding product fluid through the corresponding outlet 3 and 6 in the course of the advance movement. The pistons K1 and K2 form the components of the delivery means acting directly on the product fluid.

Connected by conventional means to each of the fluid outlets 3 and 6 is a fluid conduit 4 and 7 respectively. The fluid conduits 4 and 7 are simple catheters and are formed conventionally by a separate flexible tube with a Luer-lock tip to the ampule. Each of the separate fluid conduits 4 and 7 ports separately into a common catheter head 20.

The catheter head 20 comprises a two-part catheter head housing 21 including a flat underside or contact plate 22. Protruding from the underside at the proximal end of the catheter head housing 21 is a piercing needle N. The needle end may be generally perpendicular with respect to the underside. Within the catheter head 20, the fluid conduits run separate up to the catheter head and, formed by the single catheters 4 and 7, are merged prior to the piercing needle N. The underside of the catheter head 20 is prepared for attaching the catheter head 20 to the skin of the user. For this purpose, an adhesive coating is applied to the underside which is covered by a peel-off film. Prior to applying the catheter head 20, the user peels off this film, pricks the skin with the piercing needle at the desired site N and presses the underside of the catheter head 20 against the skin. In this,way, the catheter head 20 is attached to the skin and, more particularly, the piercing needle N located in place.

Blending the two differently acting insulin solutions does not take place until at the catheter head 20 so that each insulin solution can be precisely dosed, of course, within the scope of how fine dosing is possible by the delivery means.

Indicated is the possibility of using the catheter head 20 also as a port for an injector, which in the example embodiment is formed by a simple insulin syringe, although an injection pen for multiple dosing could also be used. The illustration is intended to suffice to show that the catheter head 20 in accordance with the invention may serve as a port for an infusor and simultaneously as a port for a manually activated injector by it being provided with corresponding connectors. The connector for the injector is formed by fluid guide means fluidly communicating with the piercing needle N in the catheter head 20. The fluid guide means ports into the surface of the catheter head 20 in such a direction that convenient insertion of a piercing needle, normally used as the needle of the injector, is made possible. The injection needle of the injector in this case serves, however, as the needle connecting the piercing needle N of the catheter head 20. The fluid guide means for connecting the injector is hermetically sealed by a septum, this involving a septum as known for usual catheter heads. After puncturing, the septum surrounds the needle of the injector, and, after the needle has been removed, it reseals the fluid guide means of the catheter head 20 hermetically. In accordance with the invention the catheter head 20 may also be a catheter head having only one fluid conduit from the infusor in accordance with the invention or a conventional infusor having only one ampule 2 or 5, i.e. one fluid space only. In this case, the infusor administers, for example, the normal pump insulin through the catheter head 20 and its piercing needle N. At the same time, for example, quick-acting insulin, so-called insulin analog, is injected by means of the injector comprising the injection needle by the same catheter head at the required times. For self-administering, the user can always recourse to the piercing needle N of the catheter head 20, already inserted subcutaneously by means of an injector, instead of having to re-pierce the skin every time which is psychologically not unproblematic.

Figure 2A:
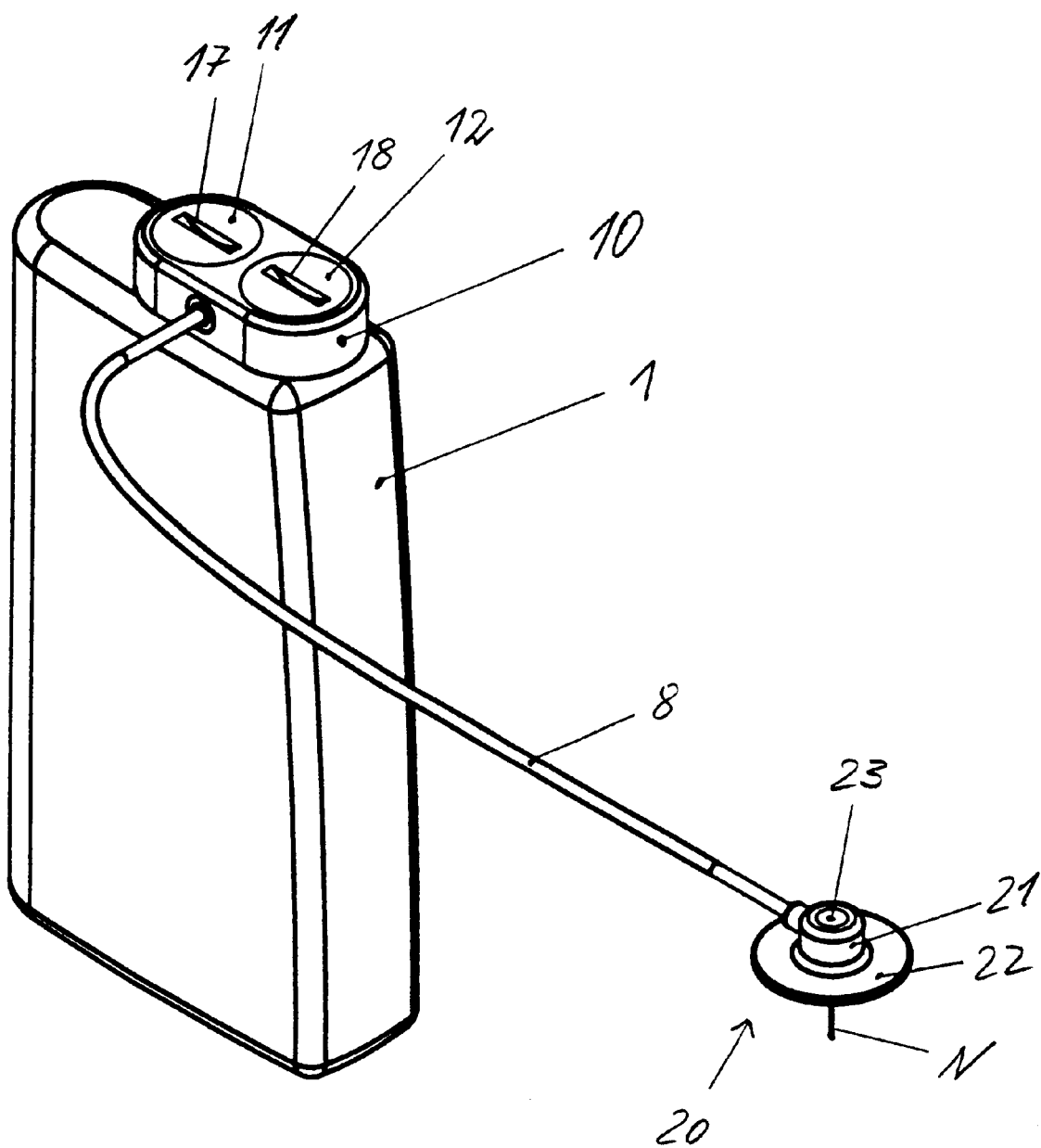
FIG. 2a is a view in perspective of a second example embodiment of an infusor, a connected catheter means and a catheter head.
Figure 2B:
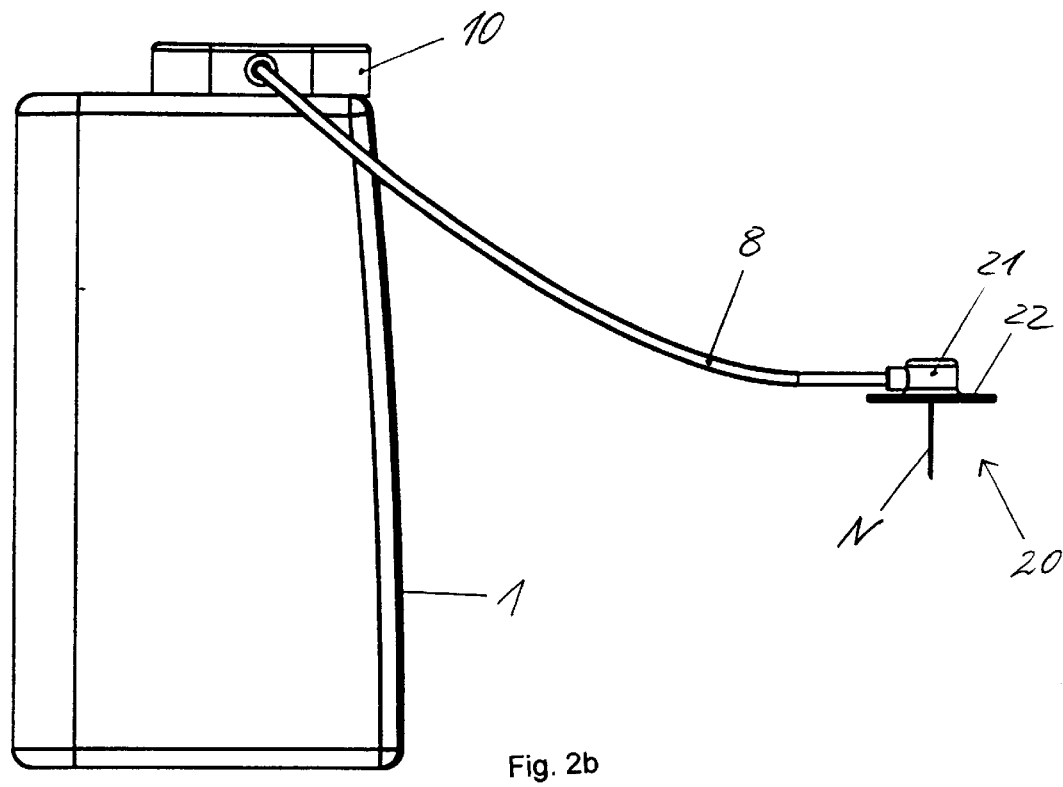
Figure 2C:
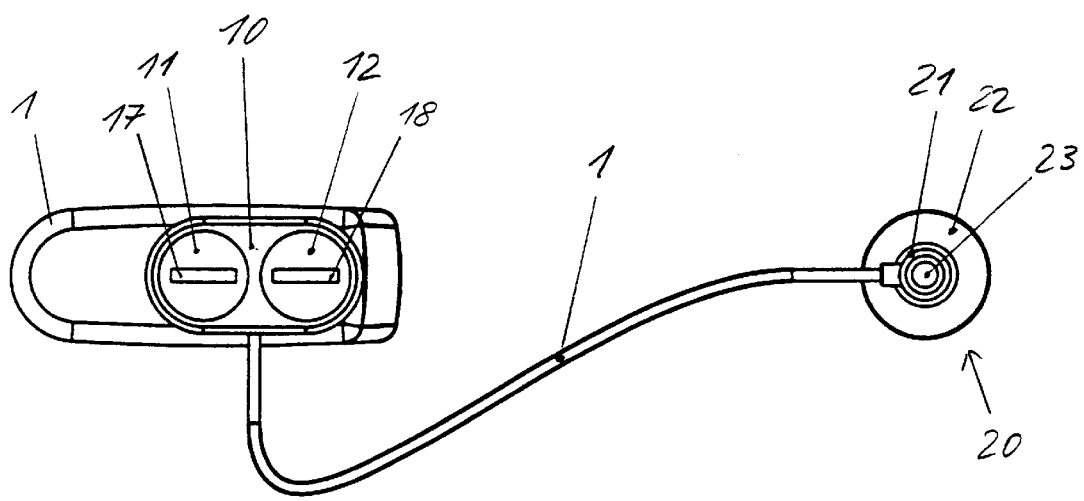
Figure 2D:
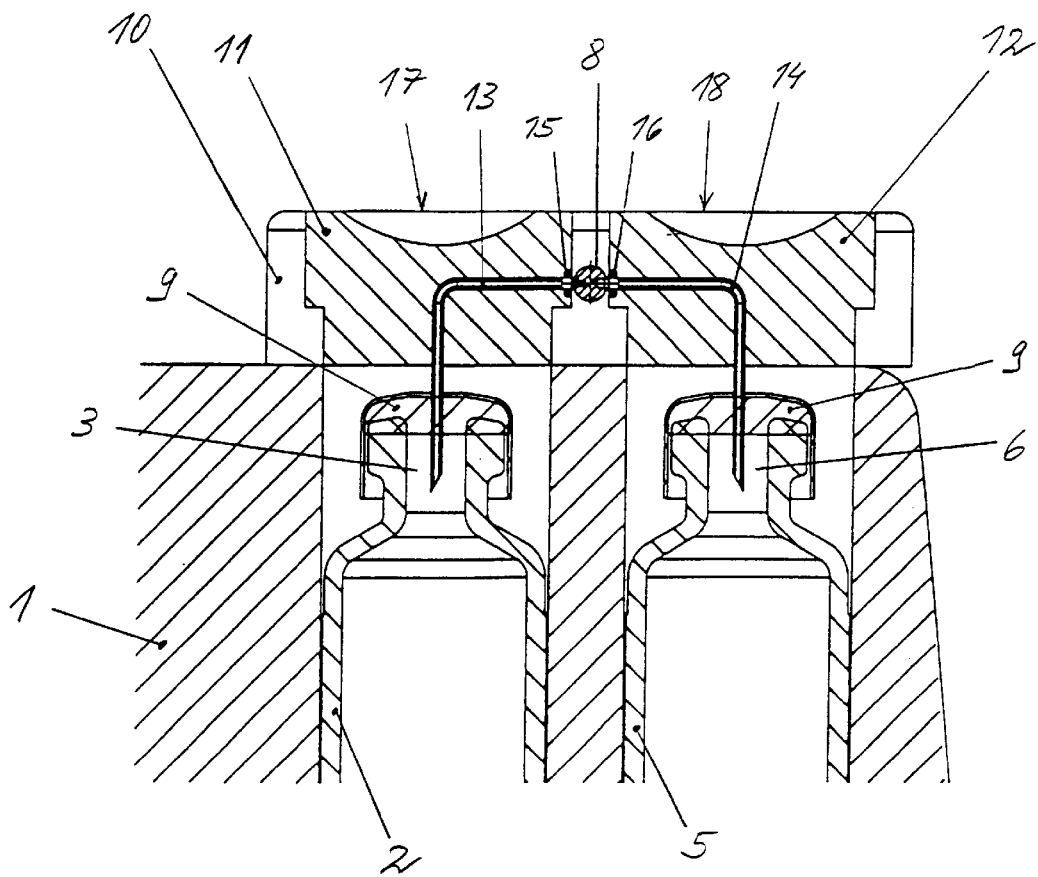
Figure 3:
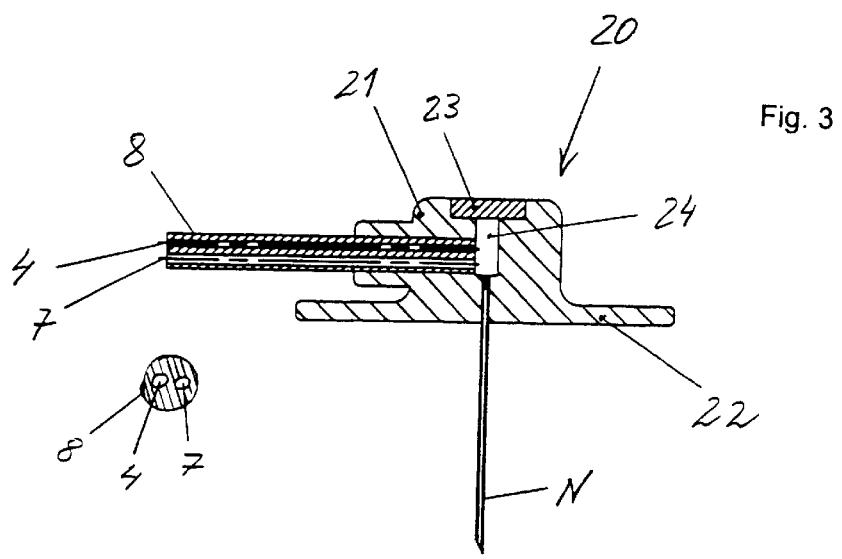

Referring now to FIGS. 2a to 3, there is illustrated an infusor, a catheter means and a catheter head in accordance with a second example embodiment. FIGS. 2a to 2c show the components of the second example embodiment in views. FIG. 2d depicts the infusor partly in a longitudinal section; FIG. 3 shows the catheter head in a longitudinal section.

The infusor as shown in FIGS. 2a to 2d differs from that shown in FIG. 1 in that its housing 1 is connected to an adapter 10, in which the fluid connectors 13 and 14 from the separate fluid spaces 2 and 5 of the infusor to the separate fluid conduits of the catheter means are integrated. In contrast to the catheter means 8 of the first example embodiment, that of the second example embodiment is configured as a two-lumen, single catheter body 8. The catheter head 20 of the second example embodiment is configured as one part.

The adapter 10 is fixedly connected to the housing 1, it forming a housing top closing off the two chutes for receiving the two ampules 2 and 5 (FIG. 2d). In the elongation of the two chutes for receiving the two ampules 2 and 5 the adapter 10 is provided with passage openings through which the ampules 2 and 5 can be inserted into the corresponding chute. Each of the passage openings of the adapter 10 is closed off by a cap 11 and 12 respectively, which in the example embodiment are identical and configured as screw caps.

In each cap 11 and 12, an angled fluid connector 13 and 14—right-angled in the examplary embodiment—is formed in each case by an angled hollow steel needle, integrated in the cap by being embedded therein. The steel needles 13 and 14 are molded in place when injection-molding the caps 11 and 12. Each of the connecting needles 13 and 14 is arranged in its cap so that it protrudes from one inner face of its cap by its needle tip into a chute for receiving one of the two ampules 2 and 5 and ports by its other, angled end into the shell surface area of its cap. Each of the porting locations of the two connecting needles 13 and 14 is provided with a sealing element 15 and 16 respectively. In the operating mode of the injector, the two porting locations with the sealing elements 15 and 16 respectively are located facing each other in the adapter 10.

The catheter body 8 is already arranged integral in the adapter 10 in its location provided for operation of the infusor, for example, molded in place. The two-lumen catheter body 8 protrudes into the adapter 10 such that a connection is formed from each separate fluid conduit of the catheter body 8 to each of the integral fluid connectors 13 and 14 when the caps 11 and 12 assume their operating position as shown in FIGS. 2a, 2c and 2d. The connecting locations between the catheter body 8 or between the separate fluid conduits thereof and the fluid connectors 13 and 14 integrated in the caps are sealed off by sealing elements 15 and 16.

Each of the caps 11 and 12 is provided with an installation aid 17 and 18 which simultaneously serve as markings evident on the outside in serving to inform the user as to the operating position of the caps 11 and 12. In the example embodiment, the installation aids 17 and 18 are configured as screw slots machined in the cap 11 and 12. In addition to the visual indication provided thereby, the caps 11 and 12 latch into place in their operating position or they are screwed into these positions up to the stop. Also conceivable is a bajonet lock, it also being possible to configure the cap as a snap-fitting cap for the adapter 10.

The sealing elements 15 and 16 are formed by elastic sealing rings which in the unloaded condition, i.e. outside of the operating positions of the cap 11 and 12 protrude slightly from the outer shell surface area and in the operating positions of the caps 11 and 12 are elastically compressed by the contact with the catheter body 8 as shown in FIG. 2d.

Inserting the ampules 2 and 5 is simple due to the adapter 10 and its caps 11 and 12. With the caps 11 and 12 removed, the ampules 2 and 5 are inserted through the adapter 10 into the respective accommodating chute in the infusor until they reach a stop. Subsequently, the two caps 11 and 12 are screwed into the adapter 10 up to the operating position as shown in FIGS. 2a, 2c and 2d. In the course of securing the caps 11 and 12, the connecting needles 13 and 14 each puncture a septum 9 with which each ampule 2 and 5 is closed. In the operating positions, i.e., in the rotary angle positions provided for the connection to the catheter body 8, the two installation aids are in alignment, and thus serve as clearly evident markings for indicating the correct rotary angle position of the caps 11 and 12. In the operating position of the caps 11 and 12, the sealing elements 15 and 16 are in sealing contact with the catheter body 8 which, in the shell portion surrounded by the sealing elements 15 and 16, comprises transverse fluid connectors to its separate fluid conduits. In this way, a separate fluid conduit is established from each ampule 2 and 5 to each fixedly arranged, separate fluid conduit of the catheter body 8.

Referring now to FIG. 3, there is illustrated the catheter head 20 of the second example embodiment in a longitudinal section. The catheter head 20 is formed integral with a catheter head housing 21 and a contact plate 22, the underside of which is in contact with the skin of the user. For fixing the catheter head 20 in place, the underside of the contact plate 22 is provided with an adhesive coating which is exposed when a peel-off film is removed.

The two-lumen catheter body 8 with its two integral separate fluid conduits 4 and 7 is embedded in the catheter head 20. The catheter body is a single piece of tubing of round or flattened cross-section of a solid material except for the two fluid conduits 4 and 7. The two separate fluid conduits 4 and 7 are guided in the catheter body 8 directly up to the fluid space formed in the catheter head 20. This fluid space, together with the part of the catheter body 8 embedded in the catheter head 20, forms the fluid guide means 24 of the catheter head 20. The needle N protruding from the underside of the catheter head 20 is guided up into the fluid space of the fluid guide means 24, i.e., the fluid space is located directly above the needle N.

The fluid space, formed in the catheter head 20, comprises a further inlet to be configured freely accessible at a free surface of the catheter head 20 as a port for a product administering device, more particularly, an injector pen or a simple syringe. This additional inlet is hermetically sealed by means of a septum 23. The additional inlet of the catheter head 20 is configured in alignment with the needle N, the needle N protruding from the underside of the catheter head 20 in the normal direction. It would be possible for the same arrangement of the additional inlet to reconfigure the needle N to protrude at an acute angle from the underside of the catheter head 20, or to arrange the inlet inclined.

Figure 4:
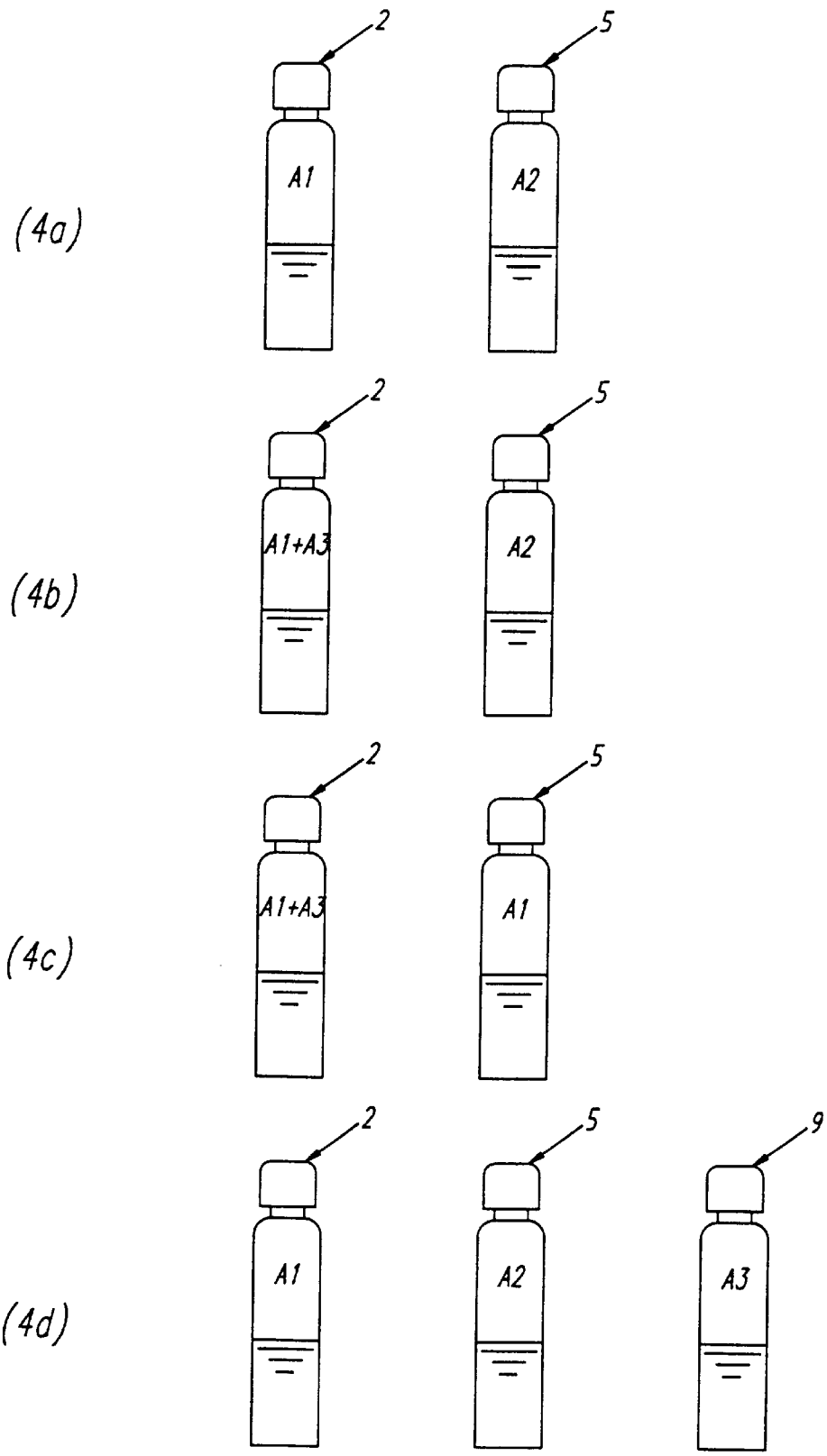
FIG. 4 illustrates various combinations of different product fluids.

Referring now to FIGS. 4a to 4d, there are illustrated insulin combinations. In the combination as shown in FIG. 4a, the ampule 2 contains normal pump insulin A1 and the ampule 5, the fast-acting insulin analog A2. The pump insulin A1 is delivered and administered quasi-continuously, i.e. at the basal rate. When using the infusor in accordance with the invention with at least two ampules, the fast-acting insulin A2 may be administered in each case as a special bolus distributed in specific doses, at specific times and, where necessary, over a specific time period. The time of administration and, where necessary, the length of time of administration and, more particularly, the dosage per special bolus may be preprogrammed in the controller of the delivery means of the infusor. In particular, it is also possible to provide administration of a special bolus as prompted spontaneously by the user.

Another combination is shown in FIG. 4b. In this particular combination, the ampule 2 of the infusor contains a blended insulin, and the ampule 5 of the infusor again contains the fast-acting insulin A2. The blended insulin is a suitable blend of a normal pump insulin A1 and a slow-acting insulin A2, a so-called delayed insulin. In this case, the blended insulin of the ampule 2 is administered at the basal rate. Due to administering the slow-acting insulin A3 in the course of delivery at the basal rate a pump failure can be better bridged.

FIG. 4c represents a combination case intended for a lengthy duration of the delivery at the basal rate while simultaneously of extreme safety should the pump fail. Since two ampules with pump insulin A1 are provided in the infusor, namely in the ampule 5 itself and as a component of the blended insulin in ampule 2, the amount of pump insulin totally available can be considerably boosted as compared to conventional infusors. On the other hand, the time available for bridging a failure of the infusor is lengthened due to the simultaneous administration of the slow-acting insulin A3 from the ampule 2. The combination case as shown in FIG. 4c is especially useful for the example case as shown in FIG. 3 in which fast-acting insulin A2 is administrated by means of a second feeder, namely the infusor. The blend ratio in the ampule 2 of the combination case as shown in FIG. 4c is preferably selected so that the delivery rates from ampules 2 and 5 are the same, thus resulting in the two ampules 2 and 5 being emptied at the same time and can be replaced at the same time.

FIG. 4d shows the combination of all three insulin types, A1, A2 and A3 each in a separate ampule. Each of the insulin types may be filled into a conventional ampule. The three ampules in this case are insertable in corresponding receiving chutes of a single infusor and, more particularly, fixed in place by means of a suitable housing closure, preferably an adapter having individual caps. The infusor is equipped with a delivery means and a controller for the delivery means suitable for administering the insulin types in sequence, in this case three. However, one of the insulin types, for example the fast-acting insulin A2, could also be administered by means of a suitable injector, in particular, by means of a catheter head in accordance with the invention. In this event, the ampule 5 would be arranged in the injector and one of the infusors shown in FIGS. 1 to 2d having two ampules can be used.

In other combinations of 4a, 4b and 4c too, one of the insulin types, in particular type A2, may be administered by means of an injector. In this case, the ampule 2 or 5 would be a component of the injector. A conventional infusor having only one single ampule could be used. A catheter head in accordance with the invention would suffice with a sole connector for the infusor and another connector for the injector.

The present invention may be embodied in other specific forms without departing from the essential spirit or attributes thereof. It is desired that embodiments described herein be considered in all respects as illustrative, not restrictive, and that reference be made to the appended claims for considering the scope of the present invention.

What is claimed is:

1. An infusor comprising:

a housing;

a reservoir accommodated in said housing for containing a product fluid to be administered, said reservoir having at least two separate fluid spaces each space having a separate fluid outlet, wherein each reservoir includes a separately actuable piston;

automated delivery means disposed within the housing and coupled with each actuable piston for an automatic, dosed delivery of said product fluid from said reservoir; and a programmable controller coupled with the automated delivery means to cause the delivery means to deliver the product fluid from the reservoir.

2. The infusor as set forth in claim 1, wherein said product fluid is deliverable optionally from said fluid spaces.

3. The infusor as set forth in claim 1, wherein, for separate conductance of said product fluid delivered form said respective fluid space, at least one separate fluid conduit is provided for each of said fluid spaces.

4. The infusor as set forth in claim 3 wherein said separate fluid conduits form an integral, multilumen catheter body.

5. The infusor as set forth in claim 3, wherein said separate fluid conduits are separate passage conduits at least up to a catheter head carrying at least one piercing needle.

6. The infusor as set forth in claim 5, wherein said catheter head encloses a fluid guide means connecting said separate fluid conduits to said at least one piercing needle.

7. The infusor as set forth in claim 5, wherein said catheter head encloses a fluid guide means connected at an outlet end with said at least one piercing needle, and comprises at least two fluid inlets fo which at least one is closed by a septum which after being punctured by a needle, seals the needle at the puncture site.

8. The infusor as set forth in claim 1 wherein in one of said at least two fluid spaces of said infusor, product fluid of a first type is contained, and in the other of said at least two fluid spaces, product fluid of another type is contained.

9. The infusor as set forth in claim 1 wherein an adapter is connectable to said housing into which said separate fluid conduits port and in which fluid connections are configured, each of which connects one of said separate fluid spaces of said infusor to one of said separate fluid conduits.

10. The infusor as set forth in claim 9, wherein said fluid connections are configured in at least one cap releasably connected to said adapter.

11. The infusor as set forth in claim 10, wherein a fluid connection is formed by a connecting needle embedded in and protruding from said cap such that it protrudes into one off said separate fluid spaces of said infusor when said cap is secured in place.

12. The infusor as set form in claim 10, wherein a sealing element is arranged at a connecting location on said cap connecting one of said separate fluid conduits at which said fluid connection of said cap ports into a cap surface.

* * * * *